United States Patent [19]

Nojima et al.

[11] Patent Number: 4,710,579

[45] Date of Patent: Dec. 1, 1987

[54] 2-(ACETOACETYLOXY)-3-(OCTADECYLOXY)PROPYL-3-TRIMETHYLAMMONIOPROPYL PHOSPHATE OR A PHARMACEUTICALLY ACCEPTABLE SALT THEREOF

[75] Inventors: Shoshichi Nojima, Tokyo; Hiroaki Nomura; Tetsuya Okutani, both of Osaka, all of Japan

[73] Assignee: Takeda Chemical Industries, Ltd., Osaka, Japan

[21] Appl. No.: 792,878

[22] Filed: Oct. 30, 1985

[30] Foreign Application Priority Data

Nov. 9, 1984 [JP] Japan .................. 59-237271
Apr. 19, 1985 [JP] Japan .................. 60-84781

[51] Int. Cl.$^4$ .............................................. C07F 9/10
[52] U.S. Cl. ........................... 558/169; 546/22; 546/23; 546/24; 544/110; 544/232; 544/337; 548/112; 548/413; 514/89; 514/92
[58] Field of Search .............. 546/22; 558/169; 514/77

[56] References Cited

U.S. PATENT DOCUMENTS 4,159,988 7/1979 Eibl et al. .......................... 549/221
4,426,525 1/1984 Hozumi et al. ...................... 546/22

FOREIGN PATENT DOCUMENTS 3212387 10/1983 Fed. Rep. of Germany ...... 558/169
55-28955 2/1980 Japan ............................... 544/243
1583661 1/1981 United Kingdom ............... 558/169

OTHER PUBLICATIONS

Catalog of Bachem Fein Chemikalien AG (1983).

Primary Examiner—Alan L. Rotman
Attorney, Agent, or Firm—Wegner & Bretschneider

[57] ABSTRACT

A compound provided by the present invention, of the formula

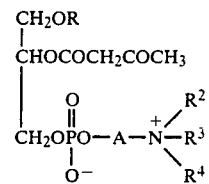

wherein $R^1$ is $C_{14-20}$ alkyl; $R^2$, $R^3$ and $R^4$ are independently hydrogen or $C_{1-5}$ alkyl, or

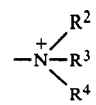

represents a cyclic ammonio group; and A is $C_{2-5}$ alkylene, and a pharmaceutically acceptable salt thereof, are useful as a anti-tumor agent.

2 Claims, No Drawings

2-(ACETOACETYLOXY)-3-(OCTADECYLOXY)-PROPYL-3-TRIMETHYLAMMONIOPROPYL PHOSPHATE OR A PHARMACEUTICALLY ACCEPTABLE SALT THEREOF

This invention relates to 2-acetoacetylglycerol derivatives, their production and use. More particularly, this invention relates to (1) a compound of the formula

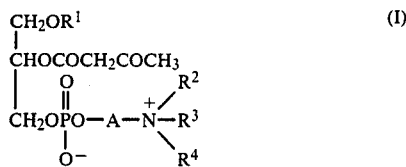

wherein $R^1$ is $C_{14-20}$ alkyl; $R^2$, $R^3$ and $R^4$ are independently hydrogen or $C_{1-5}$ alkyl, or

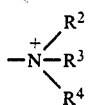

represents a cyclic ammonio group; and A is $C_{3-5}$ alkylene, and a pharmaceutically acceptable salt thereof, (2) a compound of the formula (I) wherein $R^1$ is $C_{17-20}$ alkyl; $R^2$, $R^3$ and $R^4$ are independently hydrogen or $C_{1-5}$ alkyl, or

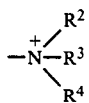

represents a cyclic ammonio group; and A is ethylene, and a pharmaceutically acceptable salt thereof, (3) a compound of the formula (I) wherein $R^1$ is tetradecyl or pentadecyl; $R^2$, $R^3$ and $R^4$ are independently hydrogen or $C_{1-5}$ alkyl, or

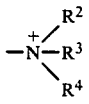

represents a cyclic ammonio group; and A is ethylene, and a pharmaceutically acceptable salt thereof, (4) methods for producing the above-mentioned compounds and (5) use of a compound of the formula (I) wherein $R^1$ is $C_{14-20}$ alkyl, $R^2$, $R^3$ and $R^4$ ae independently hydrogen or $C_{1-5}$ alkyl, or

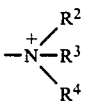

represents a cyclic ammonio group; and A is $C_{2-5}$ alkylene, and a pharmaceutically acceptable salt thereof.

Some compounds of this invention as represented by the formula (I), i.e. those of the formula (I) wherein $R^2$, $R^3$ and $R^4$ are independently hydrogen or alkyl and A is ethylene, are understood to be included in the Extent of Claim for Patent in the specification of Japanese Unexamined Patent Publication No.28955/1980, which, however, discloses only specific examples of the mere glycerol derivatives having an acyl group at the 1-position thereof, with no concrete disclosure of the compounds [glycerol derivatives having alkyl (ether linkage) in the 1-position] of this invention as represented by the formula (I). The 1-acylated glycerol derivatives as disclosed in the said gazette, whose acyl groups are readily susceptible in vivo to enzymatic hydrolysis, tend to undergo inactivation and are inferior in potency and duration of activity to the 1-alkylated glycerol derivatives. In fact, lysolecithin in concentrations about 1000 times that of PAF are known not to activate macrophage and also to be remarkably inferior in antibody forming capacity (PFC) and in vitro and in vivo antitumor activity to the corresponding alkyl ether compounds, namely lyso-PAF.

On the other hand, the compounds of this invention as represented by the formula (I) are less susceptible to such enzymatic decomposition and inactivation, and exhibit more long-lasting and potent antitumor activity.

As a natural phospholipid compound, meanwhile. there is known the platelet activating factor (PAF) as represented by the formula:

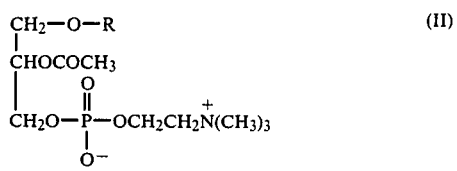

[wherein R is hexadecyl or octadecyl]. Synthetic phospholipid compounds similar to the said compound (II) are known to possess actions analogous to those of PAF, such as platelet-activating, neutrophil-activating, tissue-impairing, vessel-permeability enhancing and blood-pressure lowering actions, although to a greater or lesser extent depending on their difference in structure from the compound (II). As a natural phosphatidylcholine derivative, on the other hand, there is known the synthetic phospholipid compound as represented by the formula (e.g., the gazette of Japanese Unexamined Patent Publication No. 134027/1977):

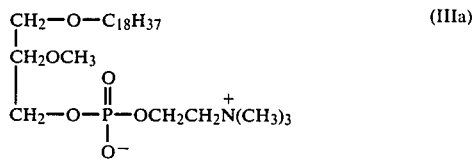

The said compound (IIIa) is known to exhibit antitumor activity unlike the natural phospholipids, while showing also platelet aggregation action [D. J. Hanahan et al.; Biochem. Biophys. Res. Commun., 99, 183 (1981)]. Such action on the platelet is likely to cause circulatory disorders, such as cerebral thrombosis and angina pectoris. In addition, both blood-pressure lowering action and topically irritating action are observed for the compound (IIIa), and these actions all constitute side effects and place restrictions on its utilization as a pharmaceutical.

In the literature [e.g., Thrombosis Res.; 30, 143 (1983)], there is described the compound of the formula:

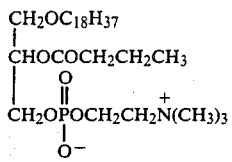

However, the said compound possesses platelet aggregation action, and its use as a pharmaceutical is restricted, as is the case with the compound (IIIa).

Furthermore, the gazette of Japanese Unexamined Patent Publication No. 67589/1982 describes the synthetic phospholipid as represented by the formula:

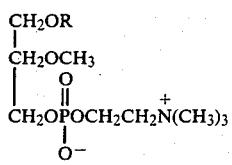

[wherein R is tridecyl or tetradecyl]. Nevertheless, the compound, with its maximum tolerant dose ($LD_{50}$) being relatively low, shows a high degree of toxicity, and in utilizing it as a pharmaceutical, there have been problems still left unsolved.

As the whole, the synthetic phospholipid compounds exhibit such actions as platelet aggregation and blood-pressure lowering actions as described previously. Since such actions constitute side effects in utilizing the synthetic phospholipid compounds as an antitumor agent and their dose capable of demonstrating the antitumor effect is extremely close to thier dose causing the side effect, they as such are very difficult to be employed as an antitumor agent.

The present inventors, with a specific view to increasing the drug therapeutic index, namely the ratio of dose causing the side-effect/dose effective for therapy, conducted repeatedly intensive research. As a result, the present inventors found that the 2-acetoacetyl-glycerol compounds of the formula (I), when administered intravenously or intraperitoneally, demonstrate outstanding antitumor activity and show macrophage activating action but surprisingly weakened actions, such as platelet aggregation action and blood-pressure lowering action, that have been considered so far to parallel the antitumor activity, resulting in by far improved drug therapeutic index, and the findings have led to the completion of this invention.

With reference to the above formula (I), the $C_{14-20}$ alkyl group represented by $R^1$ includes straight-chain or branched-chain alkyl groups, such as n-tetradecyl, n-pentadecyl, n-hexadecyl, n-heptadecyl, n-octadecyl, n-eicosanyl, 3,7,11-trimethyldodecyl and 3,7,11,15-tetramethylhexadecyl. Among others, the alkyl groups of about 15 to 19 carbon atoms are preferred.

$R^2$, $R^3$ and $R^4$ represent independently hydrogen or $C_{1-5}$ alkyl, and the said $C_{1-5}$ alkyl group includes, for example, methyl, ethyl, propyl, butyl, pentyl, preferable methyl.

The cyclic ammonio group represented by

includes, for example, pyridinio, oxazolio, thiazolio, pyridazinio, quinolinio, isoquinolinio, pyrrolidinio and piperidinio groups, and these groups may further have a substituent, such as $C_{1-4}$ alkyl (e.g., methyl, ethyl, propyl, butyl), and hydroxyl, hydroxyethyl, aminoethyl, amino(imino), carbamoyl or ureido group. Included in the above cyclic ammonio group are groups of the above formula wherein two groups of $R^2$, $R^3$ and $R^4$ form a ring together with the quaternary nitrogen atom and the remaining group is for example $C_{1-4}$ alkyl (e.g., methyl, ethyl, propyl, butyl) to thereby form e.g. specifically N-methylpyrrolidinio, N-methylmorpholinio, N-methylpiperidinio and N-methylpiperadinio groups.

The $C_{2-5}$ alkylene group represented by A includes alkylene groups such as ethylene, trimethylene, tetramethylene and pentamethylene, preferably trimethylene and tetramethylne.

In the compounds (I), there exist two kinds of the stereoisomers with R- and S-configurations exist, and their individual stereoisomers, their mixture and racemate are all included in this invention. It is to be added that the compounds (I) in some instances exist in the form of a salt represented for example by the formulae:

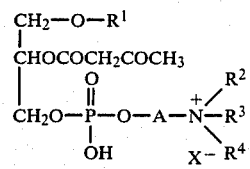

[wherein $X^{31}$ is an anion such as chlorine, bromine and iodine ions] and

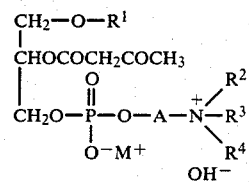

[wherein $M^+$ is an alkali metal (e.g., Na, K) ion or alkaline earth methal (e.g., Ca, Mg) ion], and such salts as pharmacologically acceptable salts are preferably.

The compound (I) of this invention can be produced, for example, by the following procedures;

A compound of the formula:

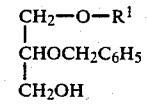

[wherein $R^1$ is as defined hereinbefore] is prepared [as synthesized by the method as described in Helv. Chim. Acta.; 65, 1059 (1982) or a method analogous thereto], whereupon on the compound (IV) is acted a compound of the formula:

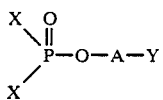 (V)

[wherein A is as defined hereinbefore; X and Y each is halogen (e.g., chlorine, bromine, iodine)], and after the reaction, water is acted on the reaction product to give a compound of the formula:

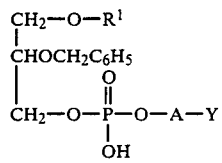 (VI)

[wherein each of the symbols is as defined hereinbefore]. The said compound (VI) is reacted with a compound of the formula:

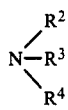 (VII)

[wherein each of the symbols is as defined hereinbefore] to give a compound of the formula:

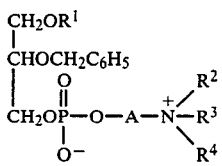 (VIII)

[wherein each of the symbols is as defined hereinbefore], and subsequently, the compound (VIII) is subjected to a per se known catalytic reduction reaction to give a compound of the formula:

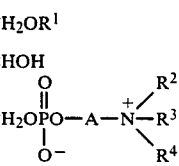 (IX)

[wherein each of the symbols is as defined hereinbefore]. The compound (IX) as obtained in the above is reacted with diketene in an inert solvent in the presence of a tertiary amine (e.g., pyridine, triethylamine, etc.) and under anhydrous conditions to give the compound (I).

The compound of the formula (I) wherein

is a secondary, tertiary or quaternary amino group can be produced by reacting the compound of the formula (I) wherein

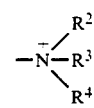

is a primary, secondary or tertiary amino group with a compound of the formula

R—I wherein R is $C_{1-5}$ alkyl, or with a compound of the formula $(R)_2SO_4$ wherein R is $C_{1-5}$ alkyl, with a compound of the formula

R—O—$SO_2$—R' wherein R is $C_{1-5}$ alkyl and R' is $C_{1-4}$alkyl or p-tolyl.

The reaction is generally carried out in a suitable solvent (e.g. acetone, benzene, toluene, dichloromethane, chloroform, tetrahydrofuran) at 0° to 200° C.

The compound (IX) can also be obtained in accordance with the method as described in the literature [e.g., Helvetica Chimica Acta, 66, 1210 (1983)] by the following procedure.

A compound of the formula:

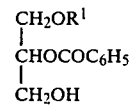 (X)

[wherein $R^1$ is as defined hereinbefore] is reacted with the compound (V), and after the reaction, water is reacted with the reaction product to give a compound of the formura:

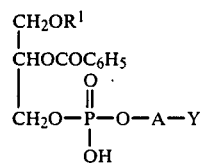 (XI)

[wherein each of the symbols is as defined hereinbefore]. The said compound (XI) is reacted with the compound (VII) to give a compound of the formula:

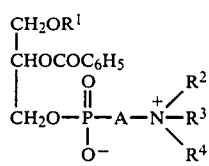 (XII)

[wherein each of the symbols is as defined hereinbefore], and subsequently, the compound (XII) is hydrolyzed to give the compound (IX). The said hydrolysis reaction is desirably carried out in the presence of a tetraalkylammonium hydroxide (e.g., tetra-n-butylammonium hydroxide).

Also, the compound (VIII) can be produced by the procedure described below.

The compound (IV) is reacted with a compound of the formula:

or phosphorus oxychloride, and water is acted on the reaction product to give a compound of the formula:

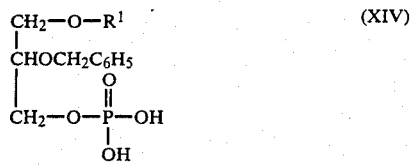

[wherein $R^1$ is as defined hereinbefore]. The said compound (XIV) is reacted with a compound of the formula:

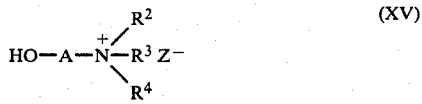

[wherein each of the symbols is as defined hereinbefore; $Z^-$ is an anion (e.g.,

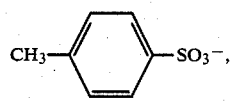

$CH_3COO^-$, $HO^-$, $Br^-$, etc.)] in the presence of a condensing agent [e.g., trichloroacetonitrile, 2,4,6-trimethylbenzenesulfonyl chloride, 2,4,6-triisopropylbenzenesulfonyl chloride, 2,4,6-trimethylbenzenesulfonyl imidazolide, 2,4,6-triisopropylbenzene-sulfonyl-3-nitroazolide, etc.) to give the compound (VIII).

In addition, the compound (VIII) can be obtained by acting phosphorus oxychloride on the compound (IV) and reacting the reaction product with the compound (XV) under anhydrous conditions, followed by action of water.

In the above, the representative procedures for producing the compound (I) are described, but it is understood that the process for producing the compound (I) as employed in this invention is not limited to these procedures.

Compounds of the formula (I) wherein A is alkylene of not less than 3 carbon atoms, and those wherein A is ethylene and $R^1$ is alkyl of 14 or 15 carbon atoms or alkyl of 17 to 20 carbon atoms are novel.

The compound (I) can be administered per se or in association with a pharmaceutically acceptable carrier.

The dosage form of preparations for the antitumor agent of the compound (I) includes a variety of pharmaceutical preparations, such as injectable solutions, tablets, solutions, and ointments, and these can be safely administered parenterally or orally.

Preparation of injectable solutions, injectable solutions for infusion, etc. is carried out in accordance with the conventional method using an aqueous solution containing adjuvants, such as physiological saline or glucose. Tablets, capsules, etc. can also be prepared in accordance with the conventional procedure. These dosage forms, for example in the case of injectable solutions, can be used through a suitable route of administration, such as intravenous and subcutaneous administration or direct application to the affected portion, depending upon the purpose of administration.

Effect

The compounds (I) are observed to be provided with remarkable diminution in side effects (e.g., platelet aggregation action, blood-pressure lowering action, vessel permeability increasing action, tissue impairing action) but enhancement in principal actions (e.g., antitumor action, macrophage activating action), and can be administered to tumor-bearing warm-blooded animals as a safe antitumor agent. The method of administration, route of administration and amount of administration can be suitably selected, whereby their amount to be administered to tumor-bearing warm-blooded animals is normally in the range of 0.1 to 150 mg/kg (body weight) as the compound (I), preferably in the range of 2 to 50 mg/kg (body weight). With reference to the frequency of administration, the said pharmaceutical preparations are applied at a rate of about once to three times a day, or at the time intervals of 2 to 7 days. Also, they can be injected intravenously for infusion over a prolonged period of time in order to maintain the concentration of the medicinal substance in the tissue at a required level for a long period of time.

EXAMPLES

REFERENCE EXAMPLE 1

3-Hydroxypropyltrimethylammonium tosylate

In 100 ml of triethylamine was dissovled 76 g (1.0 mole) of 1,3-propanediol, and 95 g (0.50 mole) of tosyl chloride was added to the solution, followed by stirring at room temperature overnight. The reaction mixture was concentrated under reduced pressure, and 800 ml of dichloromethane was added to the residue. The resulting mixture was washed with 150 ml of water, 120 ml of 1N hydrochloric acid and 150 ml of water, successively, and dried over anhydrous magnesium sulfate. The desiccating agent was filtered off and the filtrate was concentrated under reduced pressure. The residue was subjected to column chromatography of silica gel (600 g), and eluted with dichloromethane-methanol (96:4). The desired fracticns were concentrated under reduced pressure to give 1,3-propanediol monotosylate as a colorless oily material. Yield 86.9 g (yield: 78%).

NMR (90 MHz, $CDCl_3$) $\delta$:1.72 to 2.05 (2H, m), 2.43 (3H, s), 3.69 (2H, t, J=6 Hz), 4.17 (2H, t, 6 Hz), 7.33 (2H, d, J=8 Hz), 7.79 (2H, d, J=8 Hz).

IR (Neat)$cm^{-1}$: 3350, 2930, 2860, 1360, 1190, 1175, 965, 930, 815.

7 ml of 18% trimethylamine in toluene was added to 2.0 g (9.2 mmole) of the above tosylate, and the mixture was allowed to stand at room temperature for 3 days. The crystals separated out were collected by filtration, washed with toluene and dried under reduced pressure to give 3-hydroxypropyltrimethylammonium tosylate as colorless needles. Melting point: 80° C. Yield: 2.3 g (yield: 92%).

NMR (90 MHz, $CDCl_3+CD_3OD$) $\delta$:1.80 to 2.11 (2H, m), 2.37 (3H, s), 3.13 (9H, s), 3.49 to 3.73 (2H, m), 3.97 (2H, m), 7.21 (2H, d, J=8 Hz), 7.75 (2H, d, J=8 Hz).

IR (KBr)$cm^{-1}$: 3350, 1625, 1485, 1205, 1190, 1130, 1070, 1035, 1010, 915, 815, 690.

REFERENCE EXAMPLE 2

5-Hydroxypentyltrimethylammonium tosylate.

By following a procedure of Reference Example 1, 6.2 g (60 mmole) of 1,5-pentanediol and 5.7 g (30 mmole) of tosyl chloride were treated to give 1,5-pentanediol monotosylate as a colorless oily material Yield 4.1 g (yield: 53%).

NMR (90 MHz, CDCl$_3$) δ: 1.20 to 1.70 (6H, m), 2.03 (1H, s), 2.43 (3H, s), 3.53 (2H, t, J=6.5 Hz), 4.00 (2H, t, J=6.5 Hz), 7.32 (2H, d, J=8 Hz), 7.76 (2H, d, J=8Hz).

IR (Neat)cm$^{-1}$: 3330, 2930, 1590, 1350, 1185, 1170, 950, 810.

2.0 g (7.8 mmole) of the above tosylate and trimethylamine were treated to give 5-hydroxypentyltrimethylammonium tosylate as colorless needles. Melting point: 143° to 144° C. Yield: 2.3 g (yield: 95%).

NMR (90 MHz, d6-DMSO) δ: 1.20 to 1.80 (6H, m), 2.29 (3H, s), 3.03 (9H, s), 3.17 to 3.50 (4H, m), 4.40, (1H, t, J=5 Hz), 7.11 (3H, t, J=8 Hz), 7.50 (2H, t, J=8 Hz).

IR (KBr)cm$^{-1}$: 3400, 2950, 1485, 1215, 1190, 1170, 1115, 1027, 1005, 820, 680.

REFERENCE EXAMPLE 3

2-(Benzyloxy)-3-(octadecyloxy)propyl 3-trimethylammoniopropyl phosphate 2.5 g (5.8 mmole) of 2-benzyloxy-3-octadecyloxypropanol in 40 ml of chloroform was added dropwise to a mixture of 20 ml of chloroform, 0.91 g (5.9 mmole) of phosphorus oxychloride and 3.9 ml (29 mmole) of triethylamine over the period of time of 30 minutes under ice-cooling. The mixture was stirred at room temperature for 1 hour and, under ice-cooling, 2.3 g (8.4 mmole) of 3-hydroxypropyltrimethylammonium tosylate in 80 ml of pyridine was added dropwise to the mixture. The reaction mixture was stirred at room temperature for 3 days and an aqueous solution of sodium hydrogencarbonate 3.9 g) was added to the reaction mixture. The resulting mixture was concentrated under reduced pressure and 100 ml of chloroformtoluene (1:1) was added to the residue. The insoluble material was filtered off and the filtrate was concentrated under reduced pressure. 70 ml of chloroform was added to the residue and the insoluble material was filtered off. The filtrate was concentrated under reduced pressure, and the residue was subjected to column chromatography of silica gel (60 g) and eluted with chloroform-methanol-water (65:25:4). The desired fractions were concentrated to give 2-(benzyloxy)-3-(octadecyloxy)propyl 3-trimethylammoniopcopyl phosphate as a colorless solid. Yield: 2.3 g (yield: 65%).

Thin-layer chromatography [silica gel, chloroform-methanol-water (65:50:8)] Rf=0.18 single spot.

NMR (90 MHz, CDCl$_3$) δ: 0.87 (3H, m), 1.24 (30H, s), 1.45 (2H, m), 1.97 (2H, m), 3.05 9H, m), 3.26 to 4.33 (11H, m), 4.63 (2H, s), 7.29 (5H, m).

IR (KBr)cm$^{-1}$: 3420, 2920, 2850, 1620, 1480, 1465, 1260, 1120, 1050, 935, 840, 730.

REFERENCE EXAMPLE 4

2-(Benzyloxy)-3-(octadecyloxy)propyl 5-trimethyl-ammoniopentyl phosphate

By following a procedure of Reference Example 3, 2.5 g (5.8 mmole) of 2-benzyloxy-3-octadecyloxypropanol and 2.3 g (7.6 mmole) of 5-hydroxypentyltrimethylammonium tosylate obtained in Reference Example 2 were treated to give 2-(benzyloxy)-3-(octadecyloxy)propyl 5-trimethylammoniopentyl phosphate as a colorless solid material. Yield: 2.8 g (yield: 76%).

Thin-layer chromatography [silica gel, chloroform-methanol-water (65:50:8)] Rf=0.18 single spot.

NMR (90 MHz, CDCl$_3$) δ: 0.87 (3H), 1.25 (30H), 1.46 to 1.90 (8H), 3.10 (9H), 3.27 to 3.53 (4H), 3.70 to 3.95 (4H), 4.15 (3H), 4.66 (2H), 7.30 (5H).

IR (KBr)cm$^{-1}$: 3400, 2920, 2850, 1465, 1235, 1115, 1100, 1067, 820.

REFERENCE EXAMPLE 5

2-(Hydroxy)-3-(octadecyloxy)propyl 3-trimethylammoniopropyl phosphate

In 35 ml of aqueous 70% acetic acid was dissolved 2.0 g (3.3 mmole) of the 2-benzyloxy derivative obtained in Reference Example 3, and the mixture was stirred at room temperature for 3 hours in a hydrogen atonmosphere in the presence of 0.5 g of 10% palladium carbon. The catalyst was removed by filtration from the reaction mixture and the filtrate was concentrated under reduced pressure. The residue was subjected to column chromatography of silica gel (30 g) and eluted with chloroform-methanol-water (65:25:4). The desired fractions were concentrated under reduced pressure to give 2-(hydroxy)-3-(octadecyloxy) propyl 3-trimethylammoniopropyl phosphate as a colorless solid material. Yield: 1.4 g (yield: 82%).

Thin-layer chromatography [silica gel, chloroform-methanol-water (65:50:8)] Rf=0.09 single spot.

NMR (90 MHz, CDCl$_3$+CD$_3$OD) δ: 0.86 (3H, m), 1.26 (30H, s), 1.53 (2H, m), 2.10 (2H, m), 3.21 (9H, s), 3.33 to 4.06 (11H, m).

IR (KBr)cm$^{-1}$: 3410, 2920, 2845, 1630, 1465, 1220, 1115, 1050, 945, 850, 715, 680.

REFERENCE EXAMPLE 6

2-(Hydroxy)-3-(octadecyloxy)propyl 5-trimethylammoniopentyl phosphate

By following a procedure of Reference Example 5, 2.5 g (3.9 mmole) of the 2-benzyloxy derivative obtained in Reference Example 4 was treated to the desired product as a colorless solid material Yield: 1.8 g (yield: 84%).

Thin-layer chromatography [silica gel, chloroform-methanol-water (60:50:8)] Rf=0.09 single spot.

NMR (90 MHz, CDCl$_3$) δ: 0.87 (3H), 1.26 (30H), 1.40 to 2.03 (8H), 3.23 (9H), 3.30 to 3.56 (5H), 3.70 to 3.97 (4H), 4.20 to 4.67 (3H).

IR (KBr)cm$^{-1}$: 3400, 3230, 2920, 2850, 1490, 1467, 1210, 1115, 1090, 1065, 1007.

REFERENCE EXAMPLE 7

3-Hydroxypropylpyridinium tosylate

In 10 ml of pyridine was dissolved 4.0 g of 1,3-propanediol monotosylate and the mixture was stirred at 60° C. overnight. The mixture was concentrated under reduced pressure to give the desired compound as a colorless oily material. Yield: 5.6 g (quantitative).

NMR (90 MHz, DMSO-d$_6$) δ: 2.07(2H,quint,J=7 Hz), 2.26 (3H,s), 3.40(1H,s), 3.43(2H,t,J=7 Hz), 4.68 (2H,t,J=7 Hz), 7.06(2H,d,J=8 Hz), 7.48(2H,d,J=8 Hz), 8.10(2H,m), 8.56(1H,m), 9.07(2H,m).

REFERENCE EXAMPLE 8

2-(Benzoyloxy)-3-(octadecyloxy)propyl 3-pyridiniopropyl phosphate

Under ice-cooling, 4.6 g (10 mmole) of 1-octadecyl-2-benzoylglycerol (synthesized according to the procedure of Example 8) in 35 ml of chloroform was added dropwise to a mixture of 70 ml of chloroform, 1.62 g (10.5 mmole) of phosphorus oxychloride and 7.0 ml (52 mmole) of triethylamine over the period of time of 40 minutes. The resulting mixture was stirred at room temperature for 1 hour and then cooled on an ice-bath. 3.9 g (12.6 mmole) of 3-hydroxypropylpyridinium tosylate in 30 ml of pyridine was added dropwise to the mixture and the reaction mixture was stirred at room temperature overnight. An aqueous solution saturated with 7.0 g of sodium hydrogencarbonate was added to the mixture and the resulting mixture was concentrated to dryness under reduced pressure. To the residue were added 100 ml of toluene and 100 ml of dichloromethane and the insoluble material was removed by filtration. The filtrate was concentrated under reduced pressure, and then the residue was dissolved in water and subjected to chromatography on columns of 40 ml of Amberlite IRA-410 and 20 ml of Amberlite IR-120 and eluted with water and 95% hydrous tetrahydrofuran. The eluate was concentrated and the residue was subjected to column chromatography of silica gel (50 g) and eluted with chloroform-methanol-water (65:25:4). The desired fractions were concentrated to give 2-(benzoyloxy)-3-(octadecyloxy)propyl 3-pyridiniopropyl phosphate as a colorless solid material. Yield: 2.4 g (yield:37.1%).

Thin-layer chromatography [silica gel, chloroform-methanol-water (65:25:4)]: Rf=0.23 single spot.

NMR (90 MHz, CDCl$_3$) δ: 0.86(3H), 1.22(30H), 1.46(2H), 2.20(2H), 3.30 to 4.15(8H), 4.88(2H), 5.34(1H), 7.40(3H), 7.90(4H), 8.23(1H), 9.34(2H).

IR(KBr)cm$^{-1}$: 3400, 2930, 2860, 1720, 1635, 1495, 1465, 1285, 1240, 1100, 1070, 710.

REFERENCE EXAMPLE 9

2-(Hydroxy)-3-(octadecyloxy)propyl 3-pyridiniopropyl phosphate

In 5 ml of methanol was dissolved 2.4 g (3.7 mmole) of the 2-benzoyloxy derivative synthesized in Reference Example 8, and 10% tetrabutylammonium hydroxide solution (11.6 g, 4.45 mmole) was added to the mixture. The resulting mixture was stirred at room temperature for 1.5 hours and subjected to column chromatography on columns of 40 ml of Amberlite IRA-410 and 20 ml of Amberlite IR 120, successively and then eluted with 95% hydrous tetrahydrofuran. The eluate was concentrated to dryness, and the residue was subjected to chromatography on a column of silica gel (30 g) and eluted with chloroform-methanol-water (65:25:4). The desired factions were concentrated under reduced pressure, and acetone was added to the residue. The insoluble material was collected by filtration and dried to give 2-(hydroxy)-3-(octadecyloxy)propyl 3-pyridinio-propyl phosphate as a colorless solid material. Yield: 1.65 g (yield: 81.9%).

Silica gel thin-layer chromatography (Merck & Co. Art 5715): Rf=0.11 [chloroform-methanol-water (65:25:4)].

NMR (90 MHz, CDCL$_3$-CD$_3$OD) δ: 0.87(3H), 1.24(30H), 1.50(2H), 2.30(2H), 3.40(4H), 3.90(5H), 4.84(2H), 8.07(2H), 8.43(1H), 9.15(2H).

IR(KBr)cm$^{-1}$: 3350, 2925, 2850, 1635, 1490, 1470, 1230, 1070, 785.

REFERECENCE EXAMPLE 10

2-(Benzyloxy)-3-(hexadecyloxy)propyl 3-trimethylammoniopropyl phosphate

By following a procedure similar to that of Reference Example 3, the desired compound of Reference material was obtained from 2.3 g (5.7 mmole) of 2-benzyloxy-3-hexadecyloxypropanol and 2.3 g(8.4 mmole) of 3-hydroxypropyltrimethylammonium tosylate synthesized in Reference Example 1. Yield: 2.3 g (yield: 69%).

Thin-layer chromatography [silica gel, chloroform-methanol-water (65:50:8)]: Rf=0.18 single spot.

NMR (90 MHz, CDCl$_3$) δ: 0.87(3H), 1.25(26H), 1.45(2H), 1.98(2H), 3.06(9H), 3.26 to 4.34(11H), 4.64(2H), 7.30(5H).

REFERENCE EXAMPLE 11

2-(Hydroxy)-3-(hexadecyloxy)propyl 3-trimethylammoniopropyl phosphate

By following a procedure of Reference Example 5, 2.0 g (3.8 mmole) of the 2-benzyloxy derivative was treated to give the desired compound as a colorless solid material. Yield: 1.6 g (yield: 84%).

Thin-layer chromatography [silica gel, chloroform-methanol-water (65:50:8)]: Rf=0.1 single spot.

NMR (90 MHz, CDCl$_3$ +CD$_3$OD) δ: 0.87(3H), 1.25(26H), 1.50(2H), 2.10(2H), 3.22(9H), 3.33 to 4.05(11H).

REFERENCE EXAMPLE 12

2-(Benzyloxy)-3-(octadecyloxy)propyl 4-bromobutyl phosphate

In 35 ml of dry toluene were dissolved 5.86 g (13.5 mmole) of 2-benzyloxy-3-octadecyloxypropanol and 4.37 g (16.2 mmole) of 4-bromobutyl phosphorodichloridate, and the mixture was stirred at room temperature for 30 minutes. 1.28 g (16.2 mmole) of dry pyridine was added dropwise to the mixture, and the resulting mixture was stirred at room temperature for 18 hours and concentrated to dryness. To the residue was added 45 ml of water and the resulting mixture was heated under reflux for 30 minutes. After cooling, the mixture was extracted with dichloromethane and the organic layer was dried and concentrated under reduced pressure to give the desired product. Yield: 8.7 g (yield: 99.2%).

NMR (90 MHz, CDCl$_3$-CD$_3$OD) δ: 0.87(3H), 1.26(30H), 1.50(2H), 1.82 to 2.05(4H), 3.32 to 3.55(6H), 3.77(1H), 4.03(2H), 4.67(2H), 7.31(5H).

REFERENCE EXAMPLE 13

2-(Benzyloxy)-3-(octadecyloxy)propyl 4-(N-methylpyrrolidinio)butyl phosphate

In 100 ml of dry toluene was dissolved 8.70 g (13.4 mmole) of the compound obtained in Reference Example 12, and 4.56 g (53.6 mmole) of N-methylpyrrolidine was added to the mixture. The reaction mixture was stirred at 60° C. for 23 hours and then concentrated to dryness. The residue was purified by silica gel column chromatography (Merck & Co., Art 7734; eluent: chloroform-methanol-water (65:25:4) to give 3.75 g (yield: 42.8%) of the desired compound.

Silica gel thin-layer chromatography (Merck & Co., Art 5715): Rf=0.35 [chloroform-methanol-water (65:25:4)].

NMR (90 MHz, CDCl$_3$-CD$_3$OD) δ: 0.88(3H), 1.27(30H), 1.50 to 2.00(6H), 2.20(4H), 2.29(3H), 3.33 to 3.60(10H),
3.75 to 4.01(3H), 4.70(2H), 7.33(5H).

REFERENCE EXAMPLE 14

2-(Hydroxy)-3-(octadecyloxy)propyl 4-(N-methylpyrrolidinio)butyl phosphate

In a mixture of 20 ml of ethanol and 100 ml of 70% acetic acid was dissolved 3.73 g (5.7 mmole) of the compound obtained in Reference Example 13. To the mixture was added 2.0 g of 10% Pd/C and catalytic reduction was carried out. After completion of the reaction, the catalyst was removed and the filtrate was concentrated to dryness under reduced pressure to give 3.18 g (yield: 99.0%) of the desired compound.

Thin-layer chromatography [silica gel, chloroform-methanol-water (65:25:4)]: Rf=0.20 single spot.

NMR (90 MHz, CDCl$_3$-CD$_3$OD) δ: 0.87(3H), 1.27(30H),
1.61(6H), 2.22(4H), 3.03(3H), 3.47(8H), 3.77(5H).

REFERENCE EXAMPLE 15

2-(Benzyloxy)-3-(octadecyloxy)propyl 5-(pyrrolidino)pentyl phosphate

In 3 ml of trichloroethylene was dissolved 2.57 g (16.8 mmole) of phosphorus oxychloride, and 1.87 g (11.2 mmole) of 5-bromopentanol was added to the mixture with stirring on an ice-bath. After addition of 5-bromopentanol, the ice-bath was removed and the reaction mixture was stirred at room temperature for 15 hours. The reaction mixture was concentrated under reduced pressure on a water-bath keeping the temperature below 40° C. and 20 ml of toluene was added to the residue. The resulting mixture was concentrated and the residue was dissolved in 20 ml of toluene. To the resulting mixture were added 3 g (7 mmole) of 2-benzylo 3-octadecyloxypropanol and 1.8 g of pyridine with stirring at room temperature, and the mixture was stirred at room temperature for 1.5 hours. Toluene was distilled off under reduced pressure and 40 ml of water was added to the residue. After the mixture was heated under reflux for 2 hours, the mixture was cooled and separated with 80 ml of dichloromethane. Dichloromethane was distilled off and the residue was dissolved in 40 ml of ethanol. To the mixture was added 3.8 g (62.3 mmole) of pyrrolidine, and the resulting mixture was stirred at 80° C. for 2.5 hours and then concentrated to dryness under reduced pressure. The residue was dissolved in dichloromethane and washed with water, and then dichloromethane was distilled off. The residue was purified by silica gel column chromatography (methanol) to give 2.3 g (yield: 50%) of the desired compound.

Silica gel thin-layer chromatography (Merck & Co., Art. 5715): Rf=0.35 (methanol) single spot.

NMR (60 MHz, CDCl$_3$-CD$_3$OD) δ: 0.90(3H), 1.27(32H), 1.50 to 1.80(6H), 1.90 to 2.27(4H), 2.73 to 3.17(6H), 3.30 to 4.17(9H), 4.70(2H), 7.33(5H).

IR(CHCl$_3$)cm$^{-1}$: 2450, 1090, 1050, 1000

REFERENCE EXAMPLE 16

2-(Hydroxy)-3-(octadecyloxy)propyl 5-(pyrrolidino)pentyl phosphate

In 40 ml of ethanol was dissolved 2.3 g of 2-(benzyloxy)-3-(octadecyloxy)propyl 5-(pyrrolidino)pentyl phosphate, and 1.2 g of 10% palladium carbon was added to the mixture. Catalytic reduction was carried out at room temperature and atmospheric pressure under a hydrogen atmosphere. The catalyst was removed by filtration and the filtrate was concentrated under reduced pressure to give 1.75 g (yield: 90%) of the desired compound.

Silica gel thin-layer chromatography (Merck & Co., Art. 5715): Rf=0.46 [chloroform-methanol-water (65:25:4)] single spot.

NMR (60 MHz, CDCl$_3$-CD$_3$CD) δ: 0.90(3H), 1.27(32H), 1.70 to 1.87(6H), 2.00 to 2.30(4H), 2.87 to 3.27(6H), 3.33 to 3.67(4H), 3.87 to 4.20(5H).

IR(CHCl$_3$)cm$^{-1}$: 3340, 2575, 2450, 1225, 1205, 1100, 1010.

EXAMPLE 1

2-(Acetoacetyloxy)-3-(octadecyloxy)propyl 2-trimethylammonioethyl phosphate

In a mixed solvent consisting of 20 ml of pyridine and 20 ml of dichloromethane was dissolved 1.0 g (1.96 mmole) of 2-hydroxy-3-(octadecyloxy)propyl 2-trimethylammonioethyl phosphate, and 3 ml of diketene was added dropwise to the solution under stirring at 40° C. over the period of time of 30 minutes. The reaction solution was subjected to distillation, and the residue was chromatographed on a column of 15 g of silica gel, with the eluting solution (chloroform:methanol:water=65:25:4) being used, and purified. The objective fraction was concentrated to dryness, and the residue was treated with acetone and solidified to give the objective compound as a yellowish powder. Yield of 810 mg (yield: 69.4%).

Silica gel thin-layer chromatography (Art. 5715 of Merck & Co.): Rf =0.51 (chloroform:methanol:water =65:25:4).

NMR (90 MHz, CDCL$_3$) δ: 0.81(3H), 1.25(30H), 1.50 (2H), 2.26(3H), 3.39(3H), 3.50(2H), 3.33 to 4.30(10H), 5.20(1H).

EXAMPLE 2

(S)-2-Acetoacetyloxy-3-(octadecyloxy)propyl 2-trimethylammonioethyl phosphate

By following a procedure of Example 1, 928 mg (1.8 mmole) of (S)-2-hydroxy-3-(octadecyloxy)propyl 2-trimethylammonioethyl phosphate and 1 ml of diketene were treated to give 827 mg (77%) of the subject compound.

Optical rotation: $[\alpha]_D^{25°} = -0.25°$ (c=1.59, methanol).

EXAMPLE 3

2-Acetoacetyloxy-3-(octadecyloxy)propyl 2-dimethylaminoethyl phosphate

In 42 g (120 mmole) of 12.8% alcoholic dimethylamine was dissolved 7.5 g (12 mmole) of 2-benzyloxy-3-(octadecyloxy)-propyl 2-bromoethyl phosphate, and the solution was allowed to stand at room temperature for 7 days. The solvent was distilled off under reduced pressure, and the residue was dissolved in 60 ml of methanol. 3.3 g (12 mmole) of silver carbonate was added to the solution, followed by heating under reflux for 1 hour. The insoluble material was filtered off, and the filtrate was concentrated under reduced pressure. The residue was purifed by silica gel colunn chromatography (chloroform:methanol:water=65:25:4) to give 5.2 g (74%) of 2-benzyloxy-3-(octadecyloxy)propyl 2-dimethylaminoethyl phosphate.

Silica gel thin-layer chromatography (Art. 5715 of Merck & Co.): Rf =0.57 (chloroform:methancl:water=65:25:4).

NMR (60 MHz, CDCl$_3$) δ: 0.87[3H], 1.23(32H), 2.70(6H, 3.30(1H), 3.30 to 4.33(10H), 4.63(2H), 7.23(5H).

In 100 ml of ethanol was dissolved 5.2 g of the above compound, and 2 g of 5% palladium-carbon was added to the solution, followed by catalytic reduction under a stream of hydrogen at room temperature and at atmospheric pressure. The catalyst was filtered off, and the filtrate was concentrated under reduced pressure to give 3.1 g (70%) of 2-hydroxy-3-(octadecyloxy)propyl 2-dimethylaminoethyl phosphate.

Silica gel thin-layer chromatography (Art. 5715 of Merck & Co.): Rf=0.41 (chloroform:methanol:water=65:25:4).

NMR (60 MHz, CDCl$_3$-CD$_3$OD) δ: 0.90(3H), 1.27(32H), 2.90(6H), 3.20 to 4.33(11H).

To 25 ml of pyridine was added 1.49 g (3 mmole) of the above compound, and 840 mg (10 mmole) of diketene was added to the mixture, followed by stirring vigorously at 50° C. for 1 hour. 20 ml of n-propanol was added to the reaction mixture, and the reaction mixture was concentrated under reduced pressure. The residue was purified by silica gel column chromatography (chloroform:methanol:water=65:25:4) to give 1.5 g (86%) of the objective compound.

Silica gel thin-layer chromatography (Art. 5715 of Merck & Co.): Rf=0.52 (chlroform:methanol:water=65:25:4).

IR (CHCl$_3$) cm$^{-1}$: 2930, 2860, 2470, 1740, 1715, 1465, 1235, 1085, 1050.

NMR (60 MHz, CDCl$_3$) δ: 0.87(3H), 1.23(32H), 2.27(3H), 2.87(6H), 3.10 to 4.40(13H), 5.07 to 5.40(1H).

EXAMPLE 4

2-Acetoacetyloxy-3-(octadecyloxy)propyl 2-pyrrolidinoethyl phosphate

In 30 ml of toluene were dissolved 7.5 g (12 mmole) of 2-benzyloxy-3-(octadecyloxy)propyl 2-bromoethyl phosphate and 8.5 g (120 mmole) of pyrrolidine, and the mixture was stirred at 60° C. for 18 hours. The solvent was distilled off under reduced pressure, and the residue was dissolved in 60 ml of methanol. 3.3 g (12 mmole) of silver carbonate was added to the solution, and the mixture was heated under reflux for 1 hour. The insoluble material was filtered off, and the filtrate was concentrated under reduced pressure. The residue was purified by silica gel column chromatography (chloroform:methanol:water=65:25:4) to give 4.94 g (68%) of 2-benzyloxy-3-(octadecyloxy)propyl 2-pyrrolidinoethyl phosphate.

Silica gel thin-layer chormatography (Art. 5715 of Merck & Co.): Rf=0.68 (chloroform:methanol:water=65:25:4).

NMR (60 MHz, CDCL$_3$) δ: 0.87(3H), 1.23(32H), 1.97(4H), 2.93 to 4.33(15H), 4.67(2H), 7.27(5H).

In 100 ml of ethyl acetate-ethanol (1:1) was dissolved 4.94 g of the above compound, and 2 g of 5% palladium-carbon was added to the solution, followed by catalytic reduction under a stream of hydrogen at room temperature and at atmospheric pressure. The catalyst was filtered off, and the filtrate was concentrated under reduced pressure to give 3.4 g (81%) of 2-hydroxy-3-(octadecyloxy)propyl 2-pyrrolidinoethyl phosphate.

Silica gel thin-layer chormatography rt. 5715 of Merck & Co.): Rf =0.52 (chloroform:methanol:water)=65:25:4).

NMR (60 MHz, CDCL$_3$) δ: 0.87(3H), 1.23(32H), 2.07 (4H), 3.10 to 4.47(15H).

To 20 ml of pyridine were added 887 mg (1.7 mmole) of the above compound and 840 mg (10 mmole) of diketene, and the mixture was stirred vigorously at 50° C. for 1 hour. 20 ml of n-propanol was added to the reaction mixture, and the reaction mixture was concentrated under reduced pressure. The residue was purified by silica gel chromatography (chloroform:methanol:water=65:25:4) to give 742 mg (73%) of the objective compound.

Silica gel thin-layer chromatography (Avt. 5715 of Merck & Co.): Rf =0.55 (chloroform:methanol:water=65:25:4).

IR (CHCl$_3$) cm$^{-1}$: 2930, 2860, 2480, 1740, 1715, 1460, 1230, 1050.

NMR (60 MHz, CDCl$_3$) δ: 0.90(3H), 1.27(32H), 2.10(4H), 2.30(3H), 3.03 to 4.43(17H), 4.97 to 5.43(1H).

EXAMPLE 5

2-Acetoacetyloxy-3-(octadecyloxy)propyl-2-(N-methylpyrrolidinio)ethyl phosphate

In 30 ml of toluene were dissolved 7.5 g (12 mmole) of 2-benzyloxy-3-(octadecyloxy)propyl 2-bromoethyl phosphate and 10.2 g (120 mmole) of N-methylpyrrolidine, and the solution was allowed to stand at room temperature for 8 hours. The solvent was distilled off under reduced pressure, and the residue was dissolved in 60 ml of methanol. 3.3 g (12 mmole) of silver carbonate was added to the solution, followed by heating under reflux for 1 hour. The insoluble material was filtered off, and the filtrate was concentrated under reduced pressure. The residue was purified by silica gel column chromatography (chloroform:methanol:water=65:25:4) to give 3.5 g (47 %) of 2-benzyloxy-3-(octadecyloxy)-propyl 2-(N-methylpyrrolidinio)ethyl phosphate.

Silica gel thin-layer chromatography (Art. 5715 of Merck & Co.): Rf=0.49 (chloroform:methanol:water=65:25:4).

NMR (60 MHz, CDCl$_3$) δ: 0.90(3H), 1.27(32H), 2.03(4H), 3.07(3H), 3.30 to 4.40(15H), 4.67(2H), 7.27(5H).

In 60 ml of ethanol was dissolved 3.5 g of the above compound, and 1.5 g of 5% palladium-carbon was added to the solution, followed by catalytic reduction under a strea:n of hydrogen at room temperature and at atmospheric pressure. The catalyst was filtered off, and the filtrate was concentrated under reduced pressure to give 2.57 g (86%) of 2-hydroxy-3-(octadecyloxy)propyl 2-[N-methylpyrrolidinio)ethyl phospahte.

Silica gel thin-layer chromatography (Art. 5715 of Merck & Co.): Rf=0.36 (chloroform:methanol:water=65:25:4).

NMR (60 MHz, CDCl$_3$-CD$_3$OD) δ:0.90(3H), 1.27(32H), 2.03(4H), 3.13(3H), 3.30 to 4.40(15H).

To 40 ml of pyridine were added 911 mg (1.7 mmole) of the above compound and 840 mg (10 mmole) of diketene, and the mixture was stirred vigorously at 50° C. for 1 hour. 20 ml of n-propanol was added to the reaction mixture, and the reaction mixture was concentrated under reduced pressure. The residue was purified by silica gel column chromatography (chloroform:methanol:water=65:25:4) to give 665 mg (62%) of the objective compound.

Silica gel thin-layer chromatography (At. 5715 of Merck & Co.): Rf=0.49 (chloroform:methanol:water=65:25:4).

IR (CHCl$_3$) cm$^{-1}$: 2925, 2860, 1710, 1460, 1070, 1040.

NMR (60 MHz, CDCl$_3$) δ: 0.90(3H), 1.27(32H), 2.23(4H), 2.27 to 4.60(20H), 4.93 to 5.43(1H).

EXAMPLE 6

2-(Acetoacetyloxy)-3-(hexadecyloxy)propyl 2-trimethylammonioethyl phosphate

To 40 ml of pyridine was added 1.35 g (2.8 mmole) of 2-hydroxy-3-(hexadecyloxy) propyl 2-trimethylammonioethyl phosphate, and 1.74 g (20 mmole) of diketene was added to the mixture, followed by stirring vigorously at 50° C. for 1 hour. 20 ml of n-propanol was added to the reaction mixture, and the reaction mixture was concentrated under reduced pressure. The residue was purified by silica gel column chromatography (chloroform:methanol:water=65:25:4), and the product was solidified by addition of acetone to give 1.11 g (70 %) of the objective compound.

Silica gel thin-layer chromatography (Art. 5715 of Merck & Co.): Rf =0.36 (chloroform:methanol:water=65:25:4).

IR (CHCl$_3$) cm$^{-1}$: 2930, 2860, 1745, 1715, 1250, 1090, 1055, 970.

NMR (60 MHz, CDCl$_3$) δ: 0.90(3H), 1.27(28H), 2.27(3H), 3.10 to 4.50(22H), 4.87 to 5.27(1H).

EXAMPLE 7

2-Acetoacetyloxy-3-(tetradecyloxy)propyl 2-trimethylammonioethyl phosphate

To 40 ml of pyridine was added 1.36 g (3 mmole) of 2-hydroxy-3-(tetradecyloxy)propyl 2-trimethylammonioethyl phosphate, and 1.74 g (20 mmole) of diketene was added to the mixture, followed by stirring vigorously at 50° C. 20 ml of n-propanol was added to the reaction mixture, and the reaction mixture was concentrated under reduced pressure. The residue was purified by silica gel column chromatography (chloroform:methanol:water=65:25:4), and the product was solidified by addition of acetone to give 1.11 g (69%) of the objective compound.

Silica gel thin-layer chromatography (Art. 5715 of Merck & Co.): Rf=0.35 (chloroform:methanol:water=65:25:4).

IR (CHCl$_3$) cm$^{-1}$: 2930, 2860, 1740, 1720, 1255, 1090, 970.

NMR (60 MHz, CDCl$_3$) δ: 0.90(3H), 1.27(24H), 2.30(3H), 3.13 to 4.47(22H), 4.97 to 5.40(1H).

EXAMPLE 8

2-Acetoacetyloxy-3-(octadecyloxy)propyl 2-pyridinioethyl phosphate

In 200 ml of dried dichloromethane was dissolved 32.0 g (53.4 mmole) of 1-trityl-3-octadecylglycerol, and 22.4 ml of dried pyridine and then a solution of 6.7 ml (57.9 mmole) of benzoyl chloride in 100 ml of dried dichloromethane were added dropwise to the solution under stirring at 0° to 3° C. over the period of time of 30 minutes. The reaction mixture was stirred at room temperature for another 2 hours, and then concentrated under reduced pressure. 200 ml of ether was added to the residue, and the insoluble material was filtered off. The filtrate was concentrated, and the residue was purified by silica gel column chromatography (hexane:ethyl acetate=9:1) to give 28.8 g (7%) of 2-benzoyl-3-octadecyl-1-tritylglycerol as an oily material.

28.8 g (41 mmole) of the above compound and 20 ml of 1N hydrochloric acid were added to 400 ml of dioxane, followed by stirring at 80° C. for 30 minutes. Saturated aqueous sodium hydrogencarbonate solution was added to the reaction solution under ice cooling to neutralize the same, and the solvent was distilled off under reudced pressure. Dichloromethane was added to the residue, and the insoluble material was filtered off. The filtrate was dried over anhdrous sodium sulfate and concentrated under reduced pressure, and the residue was purified by silica gel column chromatography (chloroform) to give 17.15 g (93%) of 1-octadecyl-2-benzoylglycerol as an oily material.

8.98 g (20 mmole) of the above compound and 7.26 g (30 mmole) of 2-bromoethyl phosphoric acid dichloride were dissolved in 50 ml of dred toluene, and after stirring at room temperature for 30 minutes, 2.38 g (30 mmole) of dried pyridine was added dropwise to the solution. After stirring at room temperature for another 1.5 hours, 2.38 g of pyridine and 10 ml of water were added to the reaction solution, followed by stirring at room temperature overnight. The organic layer was separated, and the aqueous layer was extracted with toluene. The extract was combined with the organic layer, and the mixture was filtered. The filtrate was concentrated under reduced pressure, and the residue was purified by silica gel column chromatography [chloroform; methanol:water=65:25:4) to give 8.83 g (69%) of 2-benzoyloxy-3-(octadecyloxy)propyl 2-bromoethyl phosphate.

1.36 g (5.66 mmole) of the above compound was dissolved in 36 ml of dried pyridine, and the solution was stirred at 50° C. overnight. After stirring at 60° C. for 24 hours, the reaction solution was concentrated under reduced pressure. The residue was purified by silica gel chro:natography (chloroform:methanol:water=65:25:4) to give 2.56 g (71%) of 2-benzoyloxy-3-(octadecyloxy)propyl 2-pyridinioethyl phosphate as an oily material.

2.22 g (3.5 mmole) of the above compound was dissolved in 10 ml of methanol, and 10.9 g (4.2 mmole) of 10% aqueous solution of tetra-n-butylammonium hydroxide was added to the solution, followed by stirring at room temperature for 4.5 hours. The reaction mixture was purified by XAD-II column chromatography (eluted with water and methanol successively), and the fractions containing the objective compound were concentrated under reduced pressure. 1.57 g of the residue was purified by silica gel column chromatography (chloroform:methanol:water=65:25:4) to give 1.06 g (57%) of 2-hydroxy-3-(octadecyloxy)propyl 2-pyridinioethyl phosphate as a solid.

100 mg (0.19 mmole) of the above compound was dissolved in a mixted solution consisting of 2 ml of dried pyridine and 2 ml of dried dichloromethane under heating, and 0.5 ml of diketene was added dropwise to the solution at 25° to 35° C. The reaction solution was stirred at 23° to 38° C. for another 30 minutes and concentrated under reduced pressure. 4 ml of acetone was added to the residue, and the mixture was allowed to stand at room temperature overnight. The precipitate was collected by filtration, washed with a small amount of acetone and dried (over anhydrous phosphoric acid) under reduced pressure to give 59 mg (51%) of 2-acetoacetyloxy-3-(octadecyloxy)propyl 2-pyridinio-ethyl phosphate.

Silica gel thin-layer chromatography (Avt. 5715 of Merck & Co.): Rf=0.24 (chloroform:methanol:water =65:25:4).

NMR (90 MHz, $CDCl_{13}$)$\delta$: 0.86(3H), 1.25(30H), 1.47(2H), 2.20(3H), 3.29 to 3.53(4H), 3.45(2H), 3.88(2H), 4.31(2H), 5.01(2H), 5.14(1H), 8.05(2H), 8.43(1H), 9.28(2H).

EXAMPLE 9

2-(Acetoacetyloxy)-3-(octadecyloxy)propyl 3-trimethyl-ammoniopropyl pyosphate.

In a mixture of 30 ml of pyridine and 10 ml of dichloromethane was dissolved 800 mg of the 2-hydroxy derivative obtained in Reference Example 5, and 2 ml of diketene was added to the solution at 40° C. with stirring. After 2 hours, the solvent was distilled off from the reaction mixture and the residue was subjected to column chromatography of silica gel (15 g) and eluted with chloroform-methanol-water (65:25:4) to give the desired fractions. The fractions were concentrated under reduced pressure and the residue was treated with acetone and solidified to give 2-(acetoacetyloxy)-3-(octadecyloxy)propyl 3-trimethylammoniopropyl phosphate as an yellowish solid material. Yield: 730 mg (yield: 77%) . ? , Thin-layer chromatography [silica gel, chloroform-methanol-water (65:25:4)] Rf=0.13 single spot .

NMR (90 MHz, $CDCl_3$) $\delta$: 0.87 (3H), 1.26 (30H), 1.53 (2H), 2.13 (2H), 2.26 (3H), 3.30 (9H), 3.40 to 3.70 (6H), 3.53 (2H), 3.83 to 4.03 (4H), 5.20 (1H).

IR $(KBr)cm^{-1}$: 3420, 2920, 2840, 1740, 1715, 1465, 1235, 1090, 1055, 840.

EXAMPLE 10

2-(Acetoacetyloxy)-3-(octadecyloxy)propyl 5-trimethylammoniopentyl phosphate.

By following a procedure of Example 9, 800 mg (1.5 mmole) of the 2-hydroxy derivative obtained in Reference Example 6 was treated to give the desired product as a yellowish solid material. Yield: 750 mg (yield: 81%).

Thin-layer chromatography [silica gel, chloroform-methanol-water (65:25:4)] Rf=0.15 single spot.

NMR (90 MHz, $CDCl_3$) $\delta$: 0.90 (3H), 1.26 (30H). 1.46 (2H), 1.60 (4H), 1.90 (2H), 2.26 (3H), 3.30 (9H). 3.40 to 3.63 (6H), 3.46 (2H), 3.83 to 4.00 (4H), 5.23 (1H).

IR $(KBr)cm^{-1}$: 3400, 2920, 2850, 1740, 1715, 1665, 1235, 1090, 1070, 835.

EXAMPLE 11

2-(Acetoacetyloxy)-3-(octadecyloxy)ropyl 3-pyridiniopropyl phosphate

By following a procedure of Example 9, 1.3 g (2.39 mmole) of the 2-hydroxy derivative obtained in Reference Example 9 was treated to give the desired product as an yellow solid material Yield: 930 mg (yield: 62.1%).

Thin-layer chromatography [silica gel, chloroform-methanol-water (65:25:4)]: Rf=0.20 single spot.

NMR (90 MHz, $CDCl_3$-$CD_3OD$) $\delta$: 0.87(3H), 1.26(30H), 1.52(2H), 2.26(3H), 2.27(2H), 3.33 to 4.03(8H), 3.71(2H), 4.82(2H), 5.19(1H), 8.06(2H), 8.47(1H), 9.10(2H).

IR $(KBr)cm^{-1}$: 3400, 2920, 2850, 1735, 1715, 1630, 1490, 1460, 1230, 1090, 1060, 970, 840, 810.

EXAMPLE 12

2-(Acetoacetyloxy)-3-(hexadecyloxy)propyl 3-trimethylammoniopropyl phosphate

By following a procedure of Example 9, 800 mg (1.6 mmole) of the 2-hydroxy derivative obtained in Reference Example 11 was treated to give the desired compound as an yellowish solid material. Yield: 650 mg (yield: 70%).

Thin layer chromatography [silica gel, chloroform-methanol-water (65:25:4)]: Rf=0.12 single spot.

NMR (90 MHz, $CDCl_3$) $\delta$: 0.87(3H), 1.25(26H), 1.50(2H), 2.12(2H), 2.26(3H), 3.30(9H), 3.40 to 4.03(10H), 3.51(2H), 5.21(1H).

IR $(KBr)cm^{-1}$: 3420, 2920, 2850, 1740, 1715, 1465, 1235, 1090, 1060, 840.

EXAMPLE 13

2-(Acetoacetyloxy)-3-(octadecyloxy)propyl 4-(N-methylpyrrolidinio)butyl phosphate In a mixture of 20 ml of dry dichloromethane and 40 ml of dry pyridine was dissolved 2.00 g (3.55 mmole) of the compound obtained in Reference Example 14, and 4 ml of diketene was added to the mixture. The reaction mixture was stirred at room temperature for 1 hour and concentrated to dryness under reduced pressure. The residue was purified by silica gel column chromatography [Merck & Co., Art. 7734; eluent, chloroform-methanol-water (65:25:4)] to give 1.45 g (yield: 63.2%) of the desired compound.

Thin-layer chromatography [silica gel, chloroform-methanol-water (65:25:4)]: Rf=0.30 single spot.

NMR (90 MHz, $CDCl_3$-$CD_3OD$) $\delta$: 0.86(3H), 1.26(30H), 1.50 to 2.03(6H), 2.27(7H), 3.04(3H), 3.33 to 3.63(6H), 3.79 to 4.03(4H), 5.18(1H).

IR $(KBr)cm^{-1}$: 3425, 2920, 2855, 1740, 1715, 1650, 1465, 1230, 1065, 825.

EXAMPLE 14

2-(Acetoacetyloxy)-3-(octadecyloxy)propyl 5-(pyrrolidino)pentyl phosphate

In 20 ml of pyridine was dissolved 1.7 g (3 mmole) of 2-(hydroxy)-3-(octadecyloxy)propyl 5-(pyrrolidino)-pentyl phosphate, and 3.0 g (35.7 mmole) of diketene was added to the mixture. The mixture was stirred at 50° C. for 0.5 hour and then 30 ml of ethanol was added to the mixture. The resulting mixture was concentrated under reduced pressure and the residue was purified by silica gel column chromatography [chloroform-methanol-water (65:25:1 to 65:25:4)] to give 1.3 g (yield: 65%) of the desired compound.

Silica gel thin-layer chromatography (Merck & Co., Art. 5715): Rf=0.51 [chloroform-methanol-water (65:25:4) single spot].

NMR (60 MHz, $CDCl_3$-$CD_3OD$) $\delta$: 0.90(3H), 1.27(32H), 1.53 to 1.87(6H), 2.00 to 2.27(4H), 2.33(3H), 2.83 to 3.27 (6H), 3.43 to 4.33(9H), 5.07 to 5.40(1H) .

IR $(CHCl_3)cm^{-1}$: 2460, 1740, 1715, 1230, 1200, 1050

EXAMPLE 15

2-(Acetoacetyloxy)-3-(octadecyloxy)propyl 5-(N-methylpyrrolidinio)pentyl phosphate To 30 ml of acetone was dissolved 1.17 g (1.8 mmole) of 2-(acetoacetyloxy)-3-(octadecyloxy)propyl 5-(pyrrolidino)pentyl phosphate, and 820 mg (10 mmole) of sodium hydrogen-carbonate previously crushed in a mortar and 410 mg (2.2 mmole) of methyl paratolanesulrte were added to the solution. The mixture was stirred at 50° C. for 13 hours and acetone was distilled off under reduced pressure. In 30 ml of water was dissolved the residue and the solution was adjusted to pH 4 with 2N HCl, followed by extraction with a mixture of dichloromethane and ethanol (10:1). The solvent was distilled off and the residue was purified by silica gel column chromatography [chloroform-methanol-water (65:25:4)] to give 550 mg yield: 46%) of the desired compound.

Silica gel thin-layer chromatography (Merck & Co., Art. 5715): Rf=0.25 [chloroform-methanol-water (65:25:4)] single spot .

NMR (60 MHz, $CDCl_3$-$CD_3OD$) 6: 0.87(3H), 1.23(32H), 1.50 to 1.80(6H), 2.20 to 2.40(4H), 2.30(3H), 3.07(3H), 3.23 to 3.73(11H), 3.83 to 4.11(4H), 5.07 to 5.40(1H) .

IR $(CHCl_3)cm^{-1}$: 1735, 1715, 1235, 1200, 1090, 1065.

EXAMPLE 16 b 2-(Acetoacetyloxy)-3-(octadecyloxy)propyl 4-trimethylammoniobutyl phosphate

By following procedures of Reference Examples 1, 3 and 5 and Example 9, the desired compound was obtained as an yellow solid material.

Thin-layer chromatography [silica gel, chloroform-methanol-water (65:25:4)]: Rf=0.30 single spot.

NMR (90 MHz, $CDCl_3$-$CD_3OD$): 0.87(3H), 1.27(30H), 1.45 to 2.02(6H), 2.27(3H), 3.10(9H), 3.43(4H), 3.61(2H), 3.91(6H), 5.20(1H)

IR $(KBr)cm_{-1}$: 3410, 2920, 2850, 1740, 1715, 1630, 1465, 1225, 1090, 1065, 830.

By following a procedure of the above Reference Examples and Examples, there can be produced the following compound.

2-(Acetoacetyloxy)-3-(octadecyloxy)propyl 3-pyrrolidinopropyl phosphate 2-(Acetoacetyloxy)-3-(octadecyloxy)propyl 3-(N-methylpyrrolidinio)propyl phosphate 2-(Acetoacetyloxy)-3-(octadecyloxy)propyl 3-thiazoliopropyl phosphate 2-(Acetoacetyloxy)-3-(octadecyloxy)propyl 4-pyridiniobutyl phosphate 2-(Acetoacetyloxy)-3-(octadecyloxy)propyl 4-pyrrolidinobutyl phosphate 2-(Acetoacetyloxy)-3-(octadecyloxy)propyl 5-pyridiniopentyl phosphate 2-(Acetoacetyloxy)-3-(heptadecyloxy)propyl 2-trimethylammonioethyl phosphate 2-(Acetoacetyloxy)-3-(nonadecyloxy)propyl 3-trimethylammoniopropyl phosphate

PREPARATION EXAMPLE 1

In 1.0 l of distilled water is dissolved 50 g of the compound of Example 1, and the solution is subjected to stesile filtration and filled in 1 ml portions into 1000 vials under sterile conditions, followed by lyophilization and tight closure. On the other hand, 2 l of distilled water for injection containing 100 g of xylitol or mannitol is filled under sterile conditions in 2 ml portions into ampoules for injection, followed by fusion to prepare 1,000 ampoules of injectable solution.

On the occasion of use, the powder contained in one vial of the former is dissolved in the xylitol solution (or mannitol solution) for injection.

PREPARATION EXAMPLE 2

| Tablet: | |
|---|---|
| (1) Compound of Example 3 | 100 mg |
| (2) Lactose | 200 mg |
| (3) Corn starch | 51 mg |
| (4) Hydroxypropylcellulose | 9 mg |

The above ingredients as expressed in terms of the amount to be used per tablet are mixed and granulated in accordance with the concentional method, and after the granules are mixed with corn starch (8 mg) and magnesium stearate (2 mg), the mixture is compressed into tablets each containing 370 mg and a diameter of 9.5 mm.

PREPARATION EXAMPLE 3

The tablets of the Preparation Example 2 as described above are provided with the coating using a solution of hydroxypropylmethyl methylcellulose phthalate (14 mg) and castor oil (1 mg) in a mixed solution of acetone-ethanol (4:6) to the final concentration of 7% to manufacture the enteric-coated tablets.

EFFECT OF THE INVENTION

TEST EXAMPLE 1

Antitumor action of 2-(acetoacetyloxy)-3-(octadecyloxy)propyl ' 2-trimethylammonioethyl phosphate (Example 1)

ICR mice (a group consisting of five mice) were inoculated intraperitoneally with $1 \times 10^5$ Sarcoma 180 cells per mouse, and then given intraperitoneally 0.33 mg/mouse of the compound of Example 1 dissolved in physiological saline, three times in total, 1 hour, one day and two days after the inoculation. Also, the control compound (IIIa) was given to mice under the same conditions. Shown in Table 1 are the life-span prolongation ratio regarding died mice against the control group not treated with the drug and the number of the survived mice on the 60th day after the initiation of the test.

TABLE 1

| Tested compound | Life-span prolongation ratio (T/C %) | No. of survived mice/ No. of tested mice |
|---|---|---|
| Compound of Example 1 | 229 | 2/5 |
| Compound (IIIa) | 162 | 0/5 |
| Control group | 100 | 0/5 |

TEST EXAMPLE 2

A 0.25 mg/mouse quantity of the compound of Example 1 was given intraperitoneally to C3H/He mice (a group consisting of 5 mice) for 4 consecutive days. On the sixth day, the mice were inoculated intraperitoneally with $1 \times 10^4$ MM46 cells per mouse, and 0.25 mg/mouse of the compound of Example 1 was again given intraperitoneally to the mice for 4 consecutive days starting with the second day after the inoculation.

Also, the control compound (IIIa) was given to the mice under the same conditions. Shown in Table 2 are the life-span prolongation ratio against the control group not treated with the drug and the number of th survived mice on the 46th day after the initiation of the test.

TABLE 2

| Tested Compound | Life-span prolongation ratio (T/C %) | No. of survived mice/ No. of tested mice |
|---|---|---|
| Compound of Example 1 | 162 | (4/5) |
| Compound (IIIa) | 137 | (3/5) |
| Control group | 100 | (0/5) |

TEST EXAMPLE 3

By the same method as Test Example 2, antitumor activity of the drug was measured. The life-span prolongation ratio regarding died mice against the control group not treated with the drug and the number of the survived mice on the 47th day after the inoculation of MM46 cells are shown in Table 3.

TABLE 3

| Tested Compound | Life-span prolongation ratio (T/C %) | No. of survived mice/ No. of tested mice |
|---|---|---|
| Control group | 100 | 0/5 |
| Compound (IIIa) | 149 | 3/5 |
| Compound of Example 1 | — | 5/5 |
| Compound of Example 9 | — | 5/5 |

TEST EXAMPLE 4

Antitumor activity of the compound of Example 1
ICR mice (a group consisting of 5 mice) were inoculated subcutaneously with $1 \times 10^6$ Sarcoma 180 cells per mouse, and then given intravenously 0.1 mg/mouse and 0.3 mg/mouse of the compound of Example 1 dissolved in physiological saline, respectively, nine times in total, on the eighth, nineth, tenth, thirteenth, fourteenth, fifteenth, sixteenth, seventeenth and twentieth days after the inoculation. Also, 0.3 mg/mouse of the control compound (IIIa) was administered to mice under the same conditions. 21 days later, the tumor tissue was excised, and the weight of the tumor was measured. The tumor growth inhibition ratio as compared with that of the control grou not treated with the drug is shown in Table 4

TABLE 4

| Tested Compound | Dose (mg/mouse) | Tumor growth inhibition ratio (1-T/C), % |
|---|---|---|
| Compound of Example 1 | 0.1 | 61 |
| Same as above | 0.3 | 71 |
| Control compound (IIIa) | 0.3 | 58 |
| Control group | 0 | 0 |

TEST EXAMPLE 5

Action on platelets
[Test method and results]
The blood was collected from the male rabbit using a syringe containing 3.15% of citric acid (at a ratio of 1 part to 9 parts of the blood) s an anticoagulant, and centrifuged at 1000 r.p.m. at room temperature for 10 minutes to give platelet rich plasma (PRP). PRP was further centrifuged at 1400 r.p.m. for 15 minutes to obtain platelet pellet, which was then suspended in $Ca^{++}$ free Tyrode (containing 0.25% of gelatin) to prepare Washed PRP. 250 μl of the washed PRP was stirred at 37° C.for 2 minutes, and admixed with 25 μl of 0.2 to 0.5 mM $Ca^{++}$ solution, followed by stirring for another 30 seconds. Then, the test compound was added to the mixture to the desired concentration. Platelet aggregation was measured by use of a platelet aggregometer (manufactured by Rika Denki Co. of Japan). The results are shown in Table 5.

TEST EXAMPLE 6

Blood pressure lowering action
Seven-week old, male Sprague-Dawley rats (weighing 200 to 290 g) were anesthetized by administering intraperitoneally 60 mg/kg of pentobarbital sodium salt, and canules were inserted into the left carotid artery (for the measurment of blood pressure) and into the left femoral vein (for the intravenous administration), respectively.

The determined amount of the test compound was administered, and the drop in blood pressure (ΔmmHg) was measured. The results are shown in Table 5.

TABLE 6

| Test drug | Platelet aggregation action (%) Tested concentration (M) | | Blood pressure lowering action (Δ mmHg) Dose (μg/kg) | | | |
|---|---|---|---|---|---|---|
|  | $3 \times 10^{-7}$ | $3 \times 10^{-6}$ | 0.3 | 1 | 30 | 300 |
| Compound of Example 1 | — | 0 | — | — | — | −45 |
| Compound (IIb) | 76.3 | — | −28 | −50 | — | — |
| Compound (IIIb) | — | 77.5 | (not measured) | | | |

The compound (IIb) is a compound represented by the formula:

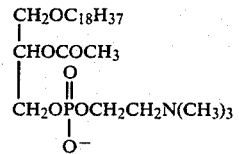

TEST EXAMPLE 7

Under the same conditions as Test Example 1, antitumor activity of the drug was measured. The life-span prolongation ratio against the control group not treated with the drug and the number of the survived mice on the 60th day after the initiation of the test are shown in Table 6.

TABLE 6

| Test Compound (Example No.) | Life-span prolongation ratio (T/C %) | No. of survived mice/ No. of tested mice |
|---|---|---|
| 3 | 215 | 1/5 |
| 4 | 182 | 0/5 |
| 5 | 268 | 0/5 |
| 7 | 185 | 0/5 |
| 8 | 280 | 0/5 |
| 9 | 194 | 3/4 |
| 10 | 169 | 0/4 |

TEST EXAMPLE 8

By the same method as Test Example 5, platelet aggregation action of the drug was measured and the concentration of the drug causing 50% platelet aggregation was calculated. The results are shown in Table 7.

TABLE 7

| Tested Compound | Concentration of Compound (M) |
| --- | --- |
| Compound of Example 2 | $>10^{-4}$ |
| Compound of Example 3 | $>10^{-4}$ |
| Compound of Example 8 | $>10^{-4}$ |
| Compound (IIb) | $1 \times 10^{-7}$ |
| Compound (IIIa) | $3 \times 10^{-5}$ |

TEST EXAMPLE 9

C3H/He mice (a group consisting of 5 mice) were inoculated intraperitoneally with $1 \times 10^4$ MM46 cells per mouse, and 0.25 mg/mouse of the tested compound was administered intraperitoneally to the mice for 4 consecutive days starting with the second day after the inoculation. Shown in Table 8 are the life-span prolongation ratio regarding died mice against the control group not treated with the drug and the number of the survived mice on the 60th day after the initiation of the test.

TABLE 8

| Tested Compound | Life-span prolongation ratio (T/C %) | No. of survived mice/ No. of tested mice |
| --- | --- | --- |
| Compound of Example 1 | 289 | 3/5 |
| Compound of Example 9 | — | 5/5 |
| Compound (IIIa) | 155 | 0/5 |
| Control group | 100 | 0/5 |

What is claimed is:
1. 2-(Acetoacetyloxy)-3-(octadecyloxy)propyl 3-trimethylammoniopropyl phosphate.
2. 2-(Acetoacetyloxy)-3-(octadecyloxy)propyl 3-trimethylammoniopropyl phosphate or a pharmaceutically acceptable salt thereof.

* * * * *